United States Patent
Vitek et al.

(10) Patent No.: US 6,506,171 B1
(45) Date of Patent: Jan. 14, 2003

(54) SYSTEM AND METHODS FOR CONTROLLING DISTRIBUTION OF ACOUSTIC ENERGY AROUND A FOCAL POINT USING A FOCUSED ULTRASOUND SYSTEM

(75) Inventors: Shuki Vitek, Haifa (IL); Naama Brenner, Haifa (IL)

(73) Assignee: InSightec-TxSonics, Ltd (IL)

(*) Notice: Subject to any disclaimer, the term of this patent is extended or adjusted under 35 U.S.C. 154(b) by 242 days.

(21) Appl. No.: 09/626,176

(22) Filed: Jul. 27, 2000

(51) Int. Cl.[7] .................................................. A61H 1/00
(52) U.S. Cl. ...................... 601/2; 601/1; 601/3; 600/439
(58) Field of Search ....................... 601/2, 3, 4; 600/439

(56) References Cited

U.S. PATENT DOCUMENTS

| | | |
|---|---|---|
| 4,441,486 A | 4/1984 | Pounds |
| 4,586,512 A | 5/1986 | Do-huu et al. |
| 4,757,820 A * | 7/1988 | Itoh ............................ 600/439 |
| 4,858,597 A | 8/1989 | Kurtze et al. |
| 4,865,042 A | 9/1989 | Umemura et al. |
| 4,938,217 A * | 7/1990 | Lele .............................. 601/3 |
| 5,247,935 A | 9/1993 | Cline et al. |
| 5,275,165 A | 1/1994 | Ettinger et al. |
| 5,291,890 A | 3/1994 | Cline et al. |
| 5,307,812 A | 5/1994 | Hardy et al. |
| 5,323,779 A | 6/1994 | Hardy et al. |
| 5,327,884 A | 7/1994 | Hardy et al. |
| 5,368,031 A | 11/1994 | Cline et al. |
| 5,368,032 A | 11/1994 | Cline et al. |
| 5,443,068 A | 8/1995 | Cline et al. |
| 5,477,736 A | 12/1995 | Lorraine |
| 5,490,840 A | 2/1996 | Uzgiris et al. |
| 5,520,188 A | 5/1996 | Hennige et al. |
| 5,526,814 A | 6/1996 | Cline et al. |
| 5,546,360 A | 8/1996 | Deegan |
| 5,590,657 A | 1/1997 | Cain et al. |
| 5,711,300 A | 1/1998 | Schneider et al. |
| 5,718,226 A * | 2/1998 | Riza ............................ 600/437 |
| 5,769,790 A | 6/1998 | Watkins et al. |
| 5,873,845 A | 2/1999 | Cline et al. |

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986.

(List continued on next page.)

Primary Examiner—George Manuel
Assistant Examiner—Runa Shah Qaderi
(74) Attorney, Agent, or Firm—Bingham McCutchen LLP (57) ABSTRACT

A focused ultrasound system includes a plurality of transducer elements disposed about and having an angular position with a central axis. Drive signals drive respective transducer elements that include phase shift values based upon the angular position of each respective transducer element. The phase shift values are based upon an oscillation function that oscillates about the central axis between minimal and maximal phase shift values such that a first on-axis focal zone and a second off-axis focal zone are created. An amplitude and frequency of the oscillation function are controlled to adjust relative acoustic energy levels of the first and second focal zones, and to adjust a radius of the second focal zone, respectively. In addition, the drive signals include an additional predetermined phase shift based upon a radial position of each respective transducer element to adjust a focal distance of the focal zones.

29 Claims, 6 Drawing Sheets

OTHER PUBLICATIONS

Todd Fjield, et al., "The Combined Concentric–Ring and Sector–Vortex Phased Array for MRI Guided Ultrasound Surgery", IEEE Transactions on Ultrasonics, Ferroelectircs and Frequency Control, vol. 44, No. 5, pp. 1157–1167, Sep. 1997.

Nathan McDannold, et al., "MRI Evaluation of Thermal Ablation of Tumors and Focused Ultrasound", JMRI vol. 8, No. 1, pp. 91–100, Jan./Feb. 1998.

Kullervo Hynynen et al., "Principles of MR–Guided Focused Ultrasound", Chapter 25, pp. 237–243.

Harvey E. Cline, Ph.D., et al., "Focused US System for MR Imaging–Guide Tumor Ablation", Radiology vol. 194, No. 3, pp. 731–738, Mar. 1995.

Todd Fjield, et al., "Low–Profile Lenses for Ultrasound Surgery", Phys. Med. Biol. 44, pp. 1803–1813, 1999.

Douglas R. Daum, et al., "Thermal Dose Optimization Via Temporal Switching in Ultrasound Surgery", IEEE Transactions on Ultrasonics, Ferroelectrics, and Frequency Control, vol. 45, No. 1, pp. 208–215, Jan. 1998.

* cited by examiner

FIG. 5D

SYSTEM AND METHODS FOR CONTROLLING DISTRIBUTION OF ACOUSTIC ENERGY AROUND A FOCAL POINT USING A FOCUSED ULTRASOUND SYSTEM

FIELD OF THE INVENTION

The present invention relates generally to systems and methods for performing noninvasive surgical procedures using focused ultrasound, and more particularly to systems and methods for controlling distribution of acoustic energy in the vicinity of a focal point, for example, to create broad, uniform necrosis volumes around the focal point using a focused ultrasound transducer array.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers that may be driven by electric signals to produce ultrasonic energy have been suggested that may be placed external to the patient but in generally close proximity to the tissue to be ablated. The transducer is geometrically shaped and positioned such that the ultrasonic energy is focused at a "focal zone" corresponding to a target tissue region within the patient, heating the target tissue region until the tissue is necrosed. The transducer may be sequentially focused and activated at a number of focal zones in close proximity to one another. This series of sonications may be used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or sectors, creating a tiling of the transducer face. The transducer elements are driven by radio frequency (RF) electrical signals at a single frequency offset in phase and amplitude. In particular, the phase and amplitude of the respective drive signals may be controlled so as to focus the emitted ultrasonic energy at a desired "focal distance," i.e., the distance from the transducer to the center of the focal zone and provide a desired energy level in the target tissue region.

In addition, the phase of the respective drive signals to each of the sectors may be controlled to create a desired size and shape for the focal zone. For example, if each of the sectors are driven with respective drive signals that are in phase with one another ("mode 0"), the ultrasonic energy may be focused substantially at a relatively narrow focal zone.

Alternatively, the sectors may be driven with respective drive signals that are in a predetermined phase relationship with one another (referred to, in Umemura et al., as "mode n"). This results in a focal zone that includes a plurality of 2n zones disposed about an annulus, i.e., generally defining an annular shape, creating a wider focus that causes necrosis of a larger tissue region within a focal plane intersecting the focal zone. One problem with such an annular focal zone, however, is that it may result in a "hole," i.e., a region within the annular focal zone that is not successfully necrosed, despite the necrosis of the surrounding tissue within the annular focal zone. This may be particularly problematic in applications where a relatively short sonication time is used such that the necrosed volume approximately matches the shape of the annular focal zone. In such applications, thermal diffusion may not play a central role in shaping the necrosed volume.

A proposed solution to this problem is temporal switching, suggested by D. R. Daum and K. Hynynen in "Thermal Dose Optimization Via Temporal Switching in Ultrasound Surgery", IEEE Transactions on Ultrasonics, Ferroelectrics, and Frequency Control, vol. 45, no. 1, pages 208–215 (January 1998). Temporal switching involves sequentially switching a transducer between various modes during a sonication to provide a more "flat" heating profile around the focal plane.

Accordingly, it would be desirable to provide systems and methods for treating a tissue region using focused ultrasound that provide a more broad, uniform volume of treated tissue and/or that reduce the risk of leaving untreated tissue within a target tissue region being treated, for example, without the complications of temporal switching.

SUMMARY OF THE INVENTION

The present invention is directed to systems and methods for performing a therapeutic procedure using focused ultrasound, and more particularly to systems and methods for controlling distribution of acoustic energy near or around a focal point, for example, to create broad, uniform necrosis volumes around the focal point.

In accordance with one aspect of the present invention, a system is provided that includes a transducer array including a plurality of transducer elements disposed about a central axis. Each transducer element has an angular position in a circumferential direction about the central axis. Drive circuitry is coupled to the transducer elements, the drive circuitry configured for providing respective drive signals to the transducer elements. A controller is coupled to the drive circuitry, the controller configured for controlling the drive circuitry to drive the transducer elements with respective drive signals that have phase shift values based upon the angular position of each respective transducer element.

The phase shift values are preferably based upon an oscillation function that oscillates between minimal and maximal phase shift values, and that repeats itself a predetermined number of times about the circumferential direction. The oscillation function has an amplitude defined by the difference between the maximal and minimal phase shift values that is not one hundred eighty (180) degrees or an integer multiple thereof. In a preferred embodiment, the oscillation function is a step function that alternates between the minimal and maximal phase shift values for driving alternate sectors about the circumferential direction of the transducer array. Alternatively, the oscillation function may approximate a sine wave or other function oscillating between the minimal and maximal phase shift values.

Preferably, the controller is configured for controlling the phase shift values such that a first focal zone is created that is located on the central axis, and a second off-axis focal zone is created around the first focal zone. More preferably, the controller is configured for controlling the phase shift values to optimally distribute acoustic energy between the first focal zone and the second focal zone in a desired manner. The controller may be also be configured for selecting the predetermined number of oscillations to adjust a radius of the second focal zone.

In addition, each of the transducer elements may have a radial position with respect to the central axis, and the minimal and maximal phase shift values, and consequently the phase shift values of respective transducer elements, may be shifted by a predetermined phase shift based upon their respective radial positions to adjust a focal distance of the focal zones of the transducer array.

In accordance with another aspect of the present invention, a method for performing a therapeutic procedure in a target tissue region of a patient is provided that includes providing a transducer array including a plurality of transducer elements disposed about a central axis, each transducer element having an angular position in a circumferential direction about the central axis. The plurality of transducer elements are driven with respective drive signals, while substantially focusing ultrasonic energy produced by the plurality of transducer elements at a focal region.

Phase shift values of the acoustic energy generated by each transducer element are controlled based upon an oscillation function wherein the phase shift values oscillate between minimal and maximal phase shift values based upon the angular position of the respective transducer element such that a first focal zone is generated that is located on the central axis, and a second off-axis focal zone is generated that is disposed around the first focal zone. The minimal and maximal phase shift values may be selected to adjust a relative maximum acoustic intensity of the first and second focal zones, and preferably such that the maximum acoustic intensity of the first focal zone is substantially the same as the maximum acoustic intensity of the second focal zone. Alternatively, the minimal and maximal phase shift values may be adjusted such that the acoustic energy delivered to the target tissue creates a more flat temperature profile, namely an optimal energy distribution that may not necessarily correspond to equal maximum acoustic intensities in the first and second focal zones.

The oscillation function may include a step function that alternates between the minimal and maximal phase shift values between adjacent sectors about the circumferential direction, or may approximate a sine wave or other periodic function. In addition, the oscillation function may be controlled such that the oscillation function repeats itself a predetermined number of times about the circumferential direction, for example, to provide a desired radius of the second focal zone.

In accordance with another aspect of the present invention, a method for performing a therapeutic procedure in a target tissue region of a patient using focused ultrasound is provided that includes providing a transducer including a central axis, and providing an acoustic lens between the transducer and a focal plane, the acoustic lens including a plurality of regions or segments disposed about the central axis of the transducer array. The transducer is driven with drive signals, while substantially focusing ultrasonic energy produced by the transducer at the focal region. The acoustic lens is controlled or otherwise allowed to create a phase shift in the acoustic energy emitted by the transducer and passing through respective regions or segments of the acoustic lens based upon an oscillation function that oscillates between the minimal and maximal phase shift values based upon an angular position of respective regions or segments of the acoustic lens such that a first focal zone is generated that is located on the central axis, and a second off-axis focal zone is generated that is disposed around the first focal zone.

Alternatively, the lens may be built in such a manner as to enable continuous changing of the phase shift values about the central axis, i.e., based upon the angular position on the surface of the lens.

Thus, a system in accordance with the present invention may generate a focal zone that includes both an on-axis component and an off-axis component that may reduce the risk of leaving unablated tissue within a target tissue region during a sonication.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
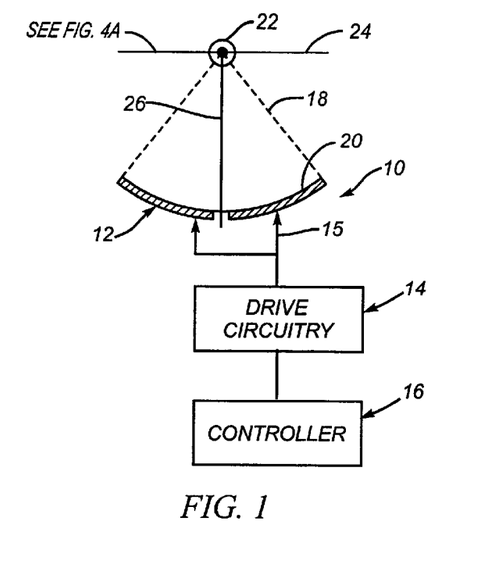
FIG. 1 is a schematic diagram of one embodiment of a focused ultrasound system, in accordance with the present invention.
Figure 2:
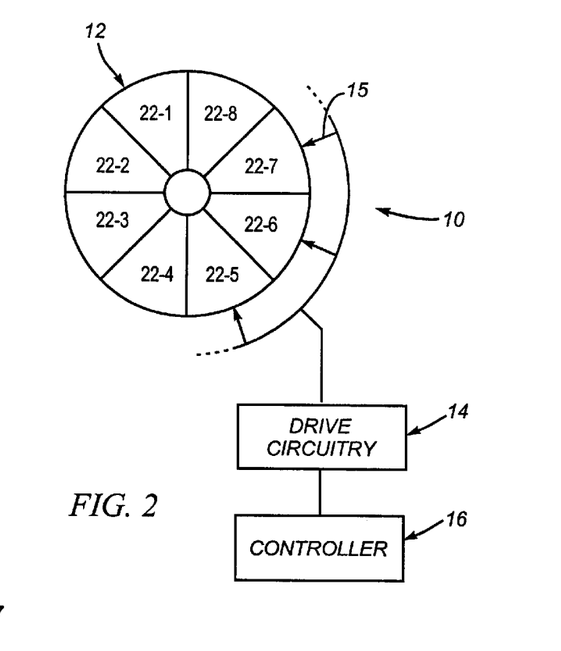
FIG. 2 is a top view of the transducer array of FIG. 1.

Turning now to the drawings, FIGS. 1 and 2 show a preferred embodiment of a system 10 for performing a therapeutic procedure using focused ultrasound, in accordance with the present invention. The system 10 generally includes a transducer 12, drive circuitry 14 for providing electrical drive signals 15 to the transducer 12, and a controller 16 for controlling the drive signals 15 provided by the drive circuitry 14. The transducer 12 is preferably a phased array ultrasound transducer formed from piezoelectric material, constructed as is known to those skilled in the art.

In one preferred embodiment, shown in FIG. 1, the transducer 12 may have a concave or bowl shape, such as a "spherical cap" shape, i.e., having a substantially constant radius of curvature 18 such that the transducer 12 has an inside surface 20 defining a portion of a sphere. Alternatively, the transducer 12 may have a substantially flat configuration (not shown), and/or may include an outer perimeter that is generally, but not necessarily truly, circular (not shown).

As shown in FIG. 2, the transducer 12 is divided into a plurality of transducer elements 22 that are disposed about a central axis 26. In the exemplary embodiment shown, the transducer 12 is divided circumferentially into a plurality of generally pie-shaped transducer elements or "sectors" 22-1 to 22-n (where n is the total number of sectors, and n=8 in FIG. 2), for example, by cutting radial lines through a piezoelectric shell (not shown). Optionally, a central on-axis opening (not shown) may be provided at the apices of the sectors. A detector, such as a hydrophone, an ultrasound receiver, or other device (not shown) may be disposed in or adjacent to the opening, and generally oriented along the central axis, for monitoring a treatment, e.g., to detect cavitation, and/or to facilitate with calibration of the system.

In alternative embodiments, the transducer elements may have a variety of geometric shapes, such as hexagons, triangles, squares, and the like, and may be disposed about the central axis 26, preferably but not necessarily, in a substantially uniform or symmetrical configuration about the central axis 26.

Although FIG. 2 shows a first exemplary embodiment of a transducer 12 that is divided into eight (8) sectors 22-1 through 22-8, the transducer may be divided any desired number, such as sixteen (16) sectors (not shown). Any spaces (not shown) between the sectors 22 may be filled with silicone rubber and the like to substantially isolate the sectors 22 from one another. The transducer 12 may also be divided radially into rings (not shown) such that each of the sectors include curved elements defining a portion of the rings. In a preferred embodiment, the transducer 12 has an outer diameter of between about 8–12 cm, a radius of curvature 18 between about 8–16 cm, and includes between 4–16 sectors 22.

Additional information on the construction of a phased array transducer appropriate for use with the present invention may be found, for example, in C. Cain and S. Umemura, "Concentric-Ring and Sector-Vortex Phased-Array Applicators for Ultrasound Hyperthermia," IEEE Transactions on Microwave Theory and Techniques, vol. MTT-34, no. 5, pages 542–551 (May 1986); and T. Fjield and K. Hynynen, "The Combined Concentric-Ring and Sector-Vortex Phased Array for MRI Guided Ultrasound Surgery," IEEE Transactions on Ultrasonics, Ferroelectrics, and Frequency Control, vol. 44, no. 5, pages 1157–1167 (September 1997), the disclosures of which are expressly incorporated herein by reference.

Returning to FIGS. 1 and 2, each of the sectors 22 is individually coupled to the drive circuitry 14 in a conventional manner. The drive circuitry 14 is configured to provide electrical drive signals 15 to the sectors 22 at one or more frequencies, preferably at radio frequencies (RF), for example, between about 0.5–10 MHz, and more preferably between about 1.0 and 2.0 MHz. When electrical drive signals 15 are provided to the sectors 22, the transducer 12 emits ultrasonic energy from its inside surface 20, as is known to those skilled in the art.

The controller 16 is coupled to the drive circuitry 14 for controlling several aspects of the drive signals 15 generated by the drive circuitry 14, such as amplitude, frequency, and/or phase. For example, the controller 16 may control the amplitude of the drive signals 15 to control the intensity of ultrasonic energy delivered by the transducer 12; in a substantially conventional manner.

In addition, the controller 16 generally controls a phase component of the respective drive signals 15 based upon an oscillation function such that the drive circuitry 14 simultaneously drives the sectors 22 with respective drive signals 15 that have a phase shift value that oscillates between a minimal phase shift value (generally zero), and a maximal phase shift value (generally a value other than an integer multiple ( . . . −3, −2, −1, 0, 1, 2, 3, . . . ) of one hundred eighty (180) degrees). The controller 16 generally controls the oscillation function such that the transducer elements 22 are driven with respective drive signals that have phase shift values based upon the angular position of the respective transducer elements. Preferably, the phase shift values vary about the circumference of the transducer 12 (or more generally in a circumferential direction about the central axis 26, e.g., for a noncircular transducer) based upon the oscillation function oscillating between the minimal and maximal phase shift values, and repeating itself a predetermined number of times about the circumference of the transducer 12 (a "frequency" of the oscillation function).

In one preferred embodiment, the controller 16 controls the phase of the drive signals 15 using a step function that alternates between the minimal and maximal phase shift values about the circumference of the transducer 12. Thus, the step function may alternate the phase of drive signals 15 applied to alternate sectors 22 around the circumference of the transducer 12 between the minimal phase shift value and the maximal phase shift value.

Figure 6:
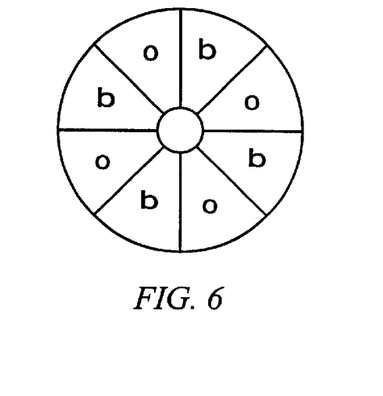
FIG. 6 is a schematic top view of the transducer array of FIG. 2, indicating an exemplary embodiment of a phase shift configuration of its sectors.

For example, as shown in FIG. 6, the odd sectors 22-1 through 22-7 may be driven with signals including a minimal phase shift value of zero (0) degrees. The even sectors 22-2 through 22-8 may be driven with signals including a maximal phase shift value "beta" that is preferably greater than zero (0) degrees, and more preferably less than one hundred eighty (180) degrees.

If the second phase shift value is zero (0) (or three hundred sixty (360)) degrees, all of the sectors 22 would be in-phase with one another, and consequently the transducer 12 would behave substantially similarly to a single element or in-phase transducer, producing an on-axis focal zone, as will be appreciated by those skilled in the art. Conversely, for a step function with the maximal phase shift value being one hundred eighty (180) degrees, the on-axis focal zone is substantially eliminated, and an annular focal zone is created, as explained further below.

Figure 4A:
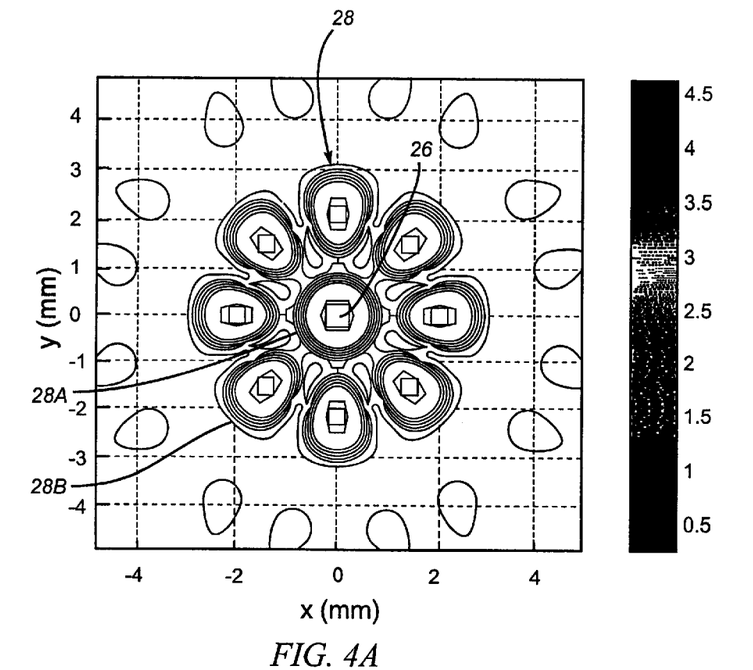
FIGS. 4A and 4B are graphs showing the acoustic intensity (in Watts/mm$^2$) generated by alternative transducer arrays, in their respective focal planes.

Turning to FIGS. 1 and 4A, during operation of the system 10, the minimal and maximal phase shift values of the step function are selected by the controller 16 (or by the user and entered into the controller 16) to create a focal zone 28 around a focal plane 24 that includes a first focal zone 28A located on the central axis 26 of the transducer 12 (an "on-axis" focal zone), and a second substantially annular-shaped focal zone 28B that is disposed concentrically around the central axis 26 and the first focal zone 28A (an "off-axis" focal zone).

The controller 16 may control an "amplitude" or relative phase shift between the minimal and maximal phase shift values of the step function to adjust an acoustic energy intensity of the first focal zone 28A with respect to an acoustic energy intensity of the second focal zone 28B. For example, turning to FIGS. 5A–5D, the resulting acoustic energy intensity profiles are shown for several amplitudes "beta," i.e., where the maximal phase shift value is "beta" and the minimal phase shift value is zero (0). In a preferred embodiment, the controller 16 may control the step function such that an "thermal dose" distribution, e.g., substantially equivalent distribution, is provided between the first focal zone 28A and the second focal zone 28B. "Thermal dose" is defined, for example, in the D. R. Daum and K. Hynynen article referenced above, the disclosure of which is expressly incorporated herein by reference, and involves consideration of temperature, sonication time, diffusion characteristics of the tissue being treated, and the like in determining damage to the tissue, as will be appreciated by those skilled in the art.

Figure 5A:
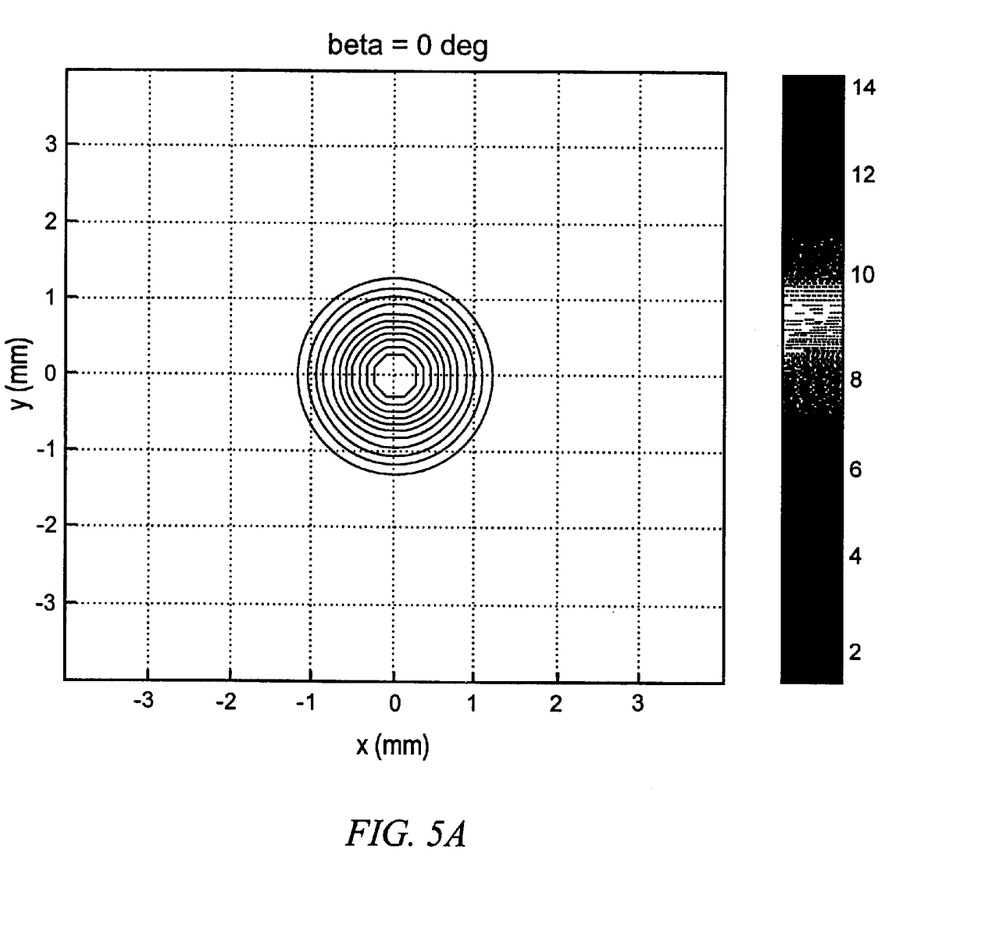
FIGS. 5A–5D are graphs showing the acoustic intensity in the focal plane of a transducer array for different amplitude oscillation functions, namely zero (0) degrees, one hundred seventeen (117) degrees, one hundred sixty two (162) degrees, and one hundred eighty (180) degrees, respectively.
Figure 5B:
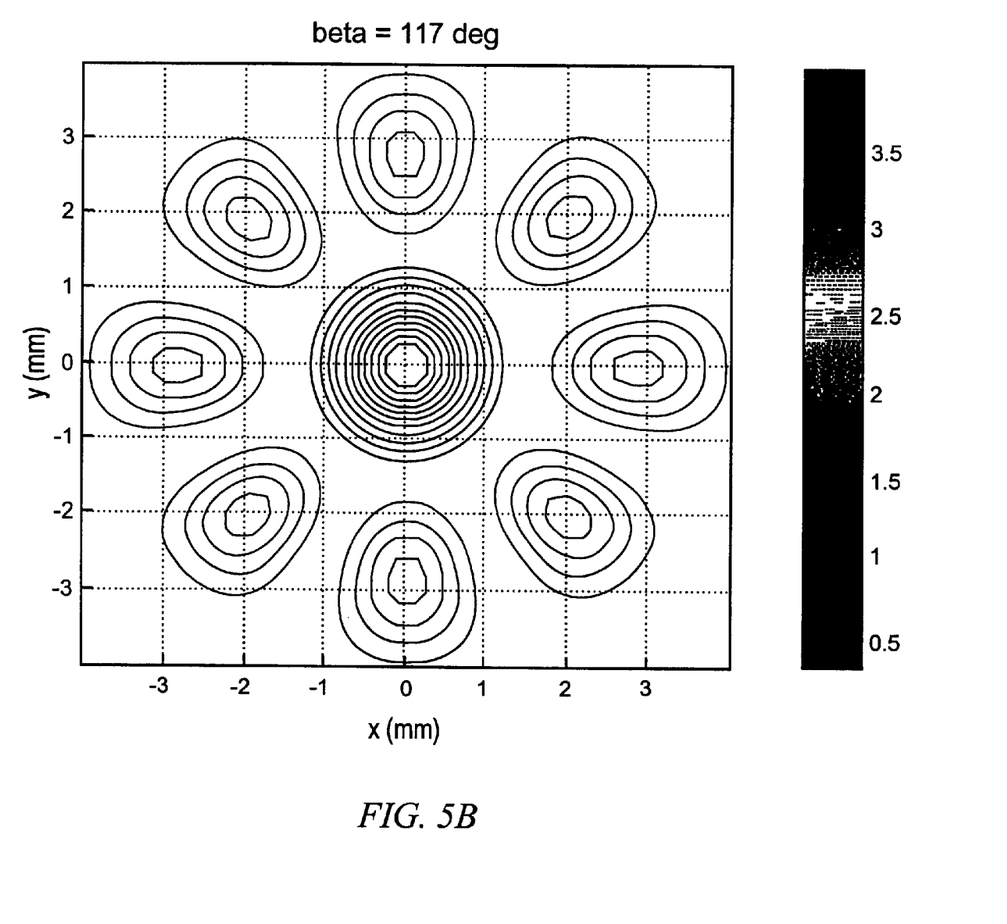
Figure 5C:
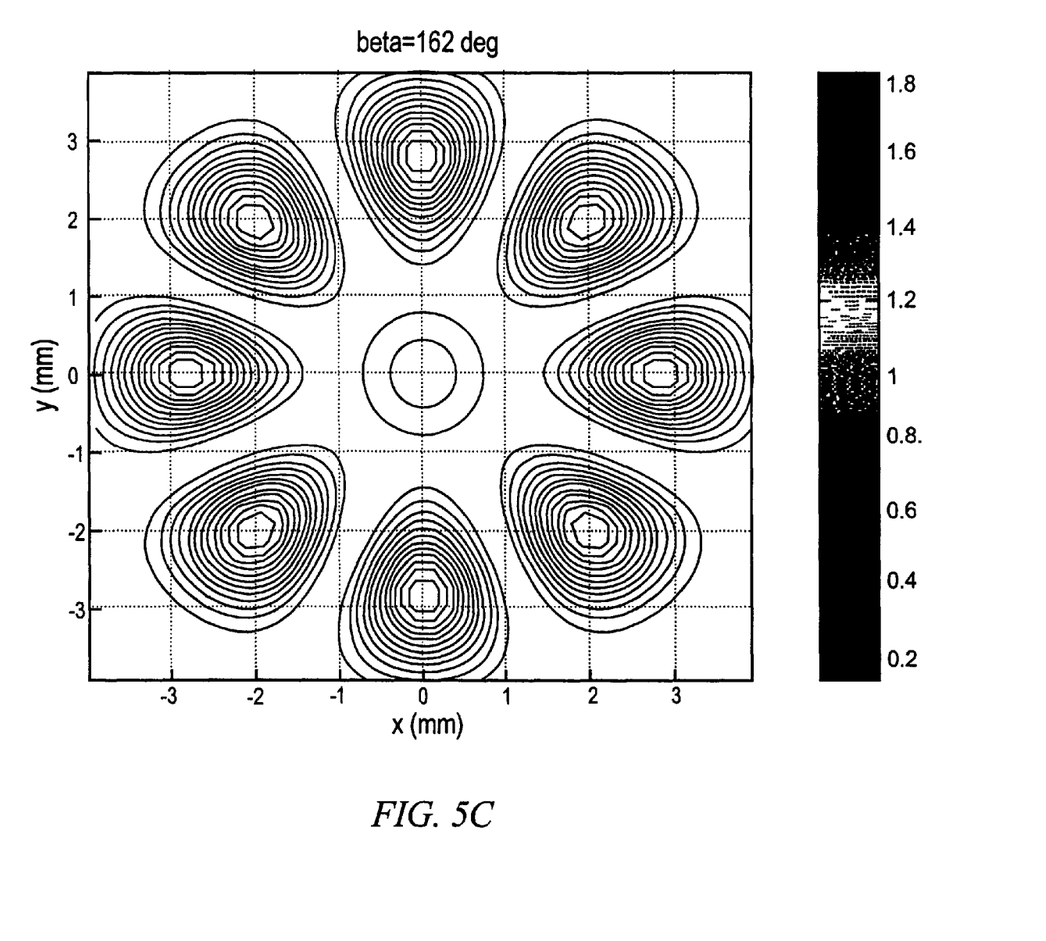
Figure 5D:
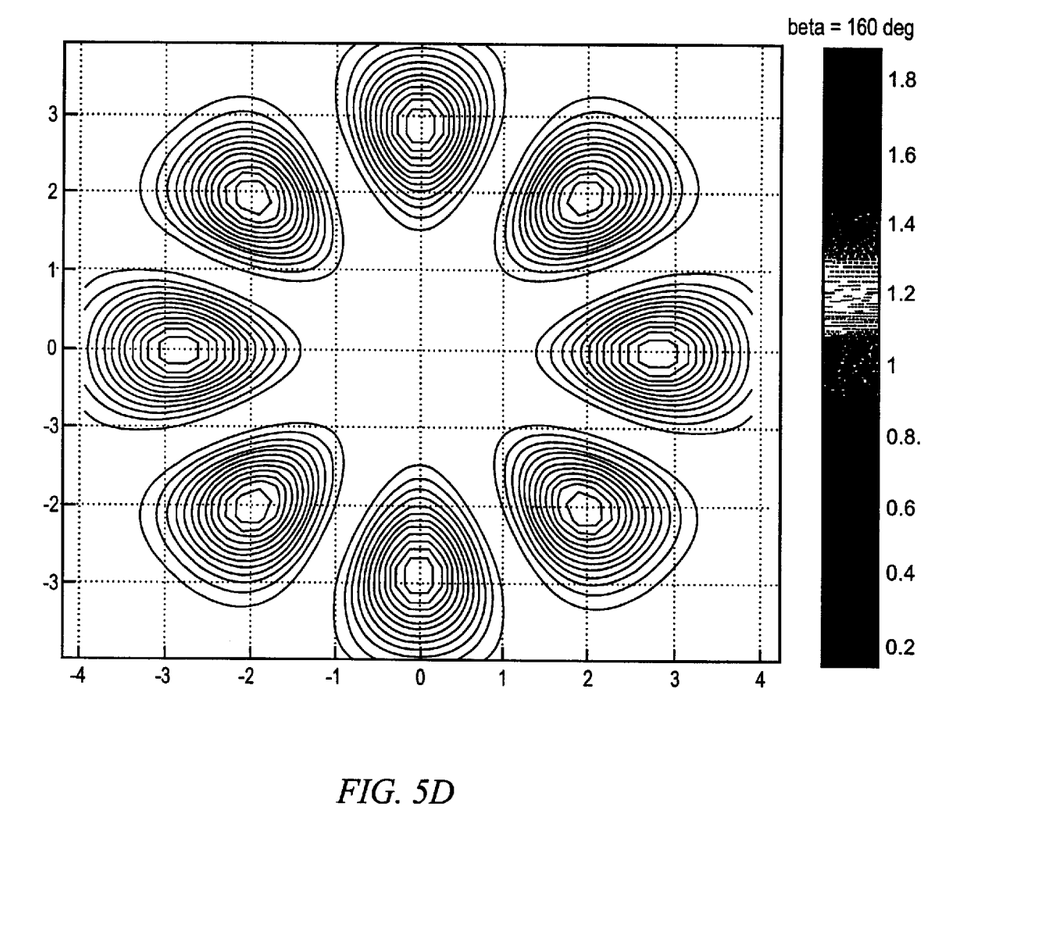

If "beta" is set at zero (0) degrees, the acoustic energy intensity of the first focal zone is maximized and the acoustic energy intensity of the second focal zone is reduced substantially to zero, similar to a single element transducer or an in-phase transducer array, as shown in FIG. 5A and described above. Conversely, if "beta" is set at one hundred eighty (180) degrees, the acoustic energy intensity of the second focal zone is maximized and the acoustic energy intensity of the first focal zone is reduced substantially to zero, as shown in FIG. 5D, thereby providing upper and lower limits for the operation of the transducer 12.

Figure 4B:
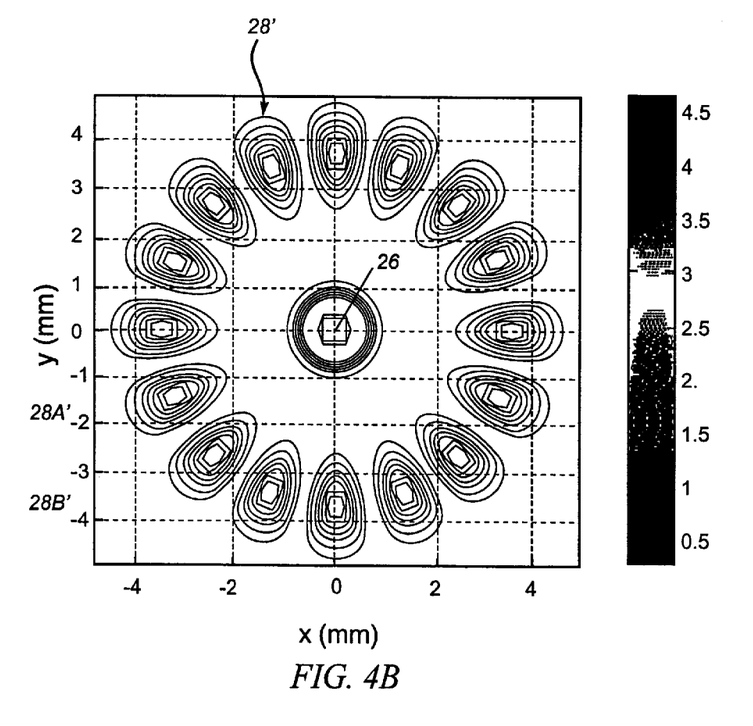

In addition, the controller 16 may also adjust the frequency M of the step function, i.e., the number of times that the step function repeats itself in a single rotation about the central axis 26 (an integer greater than zero (0)), to control a radius of the second focal zone 28B around the focal plane 24. For example, FIG. 4A shows the acoustic energy intensity levels generated by a transducer array driven by an oscillation function having a frequency of M=4. The resulting acoustic energy intensity profile has a first on-axis focal zone 28A, and a second annular-shaped off-axis focal zone 28B, the latter being formed from eight (8) relatively high intensity peaks disposed about the central axis 26. If the frequency is increased to M=8, as shown in FIG. 4B, the radius of the second off-axis focal zone is substantially increased, and the second off-axis focal zone 28B is formed from sixteen (16) relatively high intensity peaks. Thus, as the frequency increases, the radius of the off axis focal zone 28B increases and the number of peaks making up the off-axis focal zone 28B also increases (and is equal to 2M).

The frequency of the circumferential oscillating phase on a multiple-element transducer array may also be adjusted by setting groups of adjacent transducer elements of a transducer array at the same phase shift value. For example, using a sixteen (16) sector transducer array, the acoustic energy distribution of FIG. 4B may be obtained using a step function with the phase shift values alternating between zero (0) and "beta" degrees between alternate individual transducer elements about the circumference of the transducer. For the same array, the acoustic energy distribution of FIG. 4A may be obtained by pairing adjacent transducer elements about the circumference of the transducer using a step function that applies phase shift values to the individual transducer elements of 0, 0, "beta," "beta," (repeated four times about the circumference). Alternatively, a frequency of M=4 may also be obtained using an eight (8) sector transducer array using a step function that alternates between zero (0) and "beta" degrees between alternate individual transducer elements.

In another preferred embodiment, the controller 16 may control the drive circuitry 14 based upon an oscillation function approximating a sine wave that oscillates between the minimal phase shift value (generally zero) and the maximum phase shift value ("beta"). As a theoretical limit, if the transducer could include an infinite number of transducer elements disposed about the central axis, the phase shift value of each respective transducer element would be defined as:

"theta"="beta"/2*(1−cos (M*"sai")), where "theta" is the phase shift value of a particular transducer element based upon its angular position "sai" about the central axis, "beta" is the maximal phase shift value (where the minimal phase shift value is zero (0), otherwise the amplitude), and M is the "frequency" of the oscillation function.

For a transducer that includes a finite number of transducer elements, the actual oscillation function may have a finite number of steps that generally follows the curve defined by the equation given above, for example, based upon the angular position of the center of each respective transducer element. Thus, for a transducer divided into eight (8) sectors, and for an oscillation function having a "beta" of one hundred sixty (160) degrees, and a frequency M=2, the phase shift value "theta" (in degrees) of each transducer element about the central axis would be 0, 80, 160, 80, 0, 80, 160, and 80, respectively.

In a further alternative, the oscillation function may include any function that oscillates between minimal and maximal phase shift values. The modeling of a more complicated oscillation function may be more difficult, but may generally result in a focal zone that includes both an on-axis component and an off-axis component, as described above.

The distribution of acoustic energy between an on-axis focal zone and an off-axis focal zone is an important feature of the present invention. A focused ultrasound system according to the present invention generates acoustic energy that does not substantially cancel either the on-axis energy or the off-axis energy at the focal zone. Such an acoustic energy distribution may ensure that an entire tissue region within a focal zone (including on-axis and off-axis focal zones) receives sufficient acoustic energy to ablate the entire tissue region. This may substantially minimize the risk of tissue within the focal zone not being completely ablated during a sonication, as may occur using an annular focal zone. This may be particularly important in applications, such as treatment of liver tumors, where relative short (approximately one (1) second) sonications may be used. During these relatively short sonications, there may be insufficient time for thermal diffusion to fill in an annular focal zone, and consequently the necrosed volume may be substantially equal to the focal zone, and on-axis tissue may not be effectively necrosed.

In a further alternative, the controller 16 may also control the phase shift of the drive signals based upon a radial position of respective transducer elements, for example, to adjust a focal distance of the focal plane (i.e., the distance from the face of the transducer to the center of the focal zone), as is known in the art. For example, in addition to being divided into sectors 22 as shown in FIG. 2, the transducer 12 may be divided into a plurality of concentric rings (not shown). The relative phase shift of each concentric ring may be offset by a predetermined value. The controller may use an oscillation function for the sectors of each ring that includes the same amplitude "beta," although the minimal and maximal phase shift values may be increased or decreased by the phase shift corresponding to the respective ring (e.g., based upon the radial position of the respective ring). For example, the sectors of a first ring may be driven using a step function that alternates between zero (0) and "beta" degrees, while the sectors of an adjacent concentric ring may be driven using a step function that alternates between ten (10) and ("beta"+10) degrees. Thus, more complicated geometries of transducer elements may fall within the scope of the present invention, with the phase shift value of each transducer element being based upon either or both of its angular position and its radial position to control the acoustic energy distribution of the focal zone and/or the focal distance, respectively.

Figure 3:
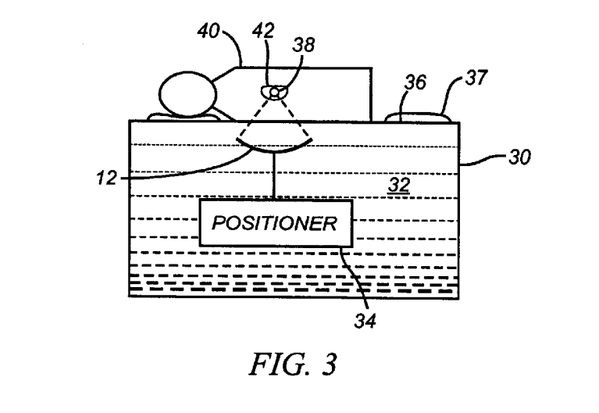
FIG. 3 is a schematic side view of a patient on a water-filled table having an ultrasound transducer array therein.

Turning to FIG. 3, the transducer 12 is generally mounted within a fluid-filled casing, such as table 30. The table 30 includes a chamber 32 filled with degassed water or similar acoustically transmitting fluid. The transducer 12 is preferably connected to a positioning system 34 that moves the transducer 12 within the chamber 32, and consequently mechanically adjusts the focal zone 38 of the transducer 12. For example, the positioning system 34 may be configured to move the transducer 12 within the chamber 32 in any one of three orthogonal directions, e.g., horizontally forward and backward, horizontally side-to-side, and vertically. U.S. Pat. No. 5,247,935 issued to Cline et al. and U.S. Pat. No. 5,275,165 issued to Ettinger et al., the disclosures of which are expressly incorporated herein by reference, disclose exemplary positioning systems that may be used.

Alternatively, the positioning system 34 may pivot the transducer 12 about a fixed point within the chamber 32, i.e., to change the angle of the transducer 12 and consequently the focal zone 38 with respect to a horizontal plane (not shown). In this alternative, the focal distance of the transducer 12 may be controlled electronically by changing the phase and/or amplitude of the drive signals 15 provided to the transducer 12, as described above. In further alternatives, the positioning system 34 may move the transducer 12 in a horizontal plane perpendicular to the line of propagation (not shown), with the depth controlled electronically, or other combinations of mechanical and electronic positioning may be used.

The top of the table 30 includes a flexible membrane 36 that is substantially transparent to ultrasound, such as a mylar plastic or polyvinyl chloride (PVC) sheet. A fluid-filled bag or cushion 37 is generally provided along the top of the table 30 that may conform easily to the contours of a patient 40 placed on the table. In a further alternative, the transducer 12 may be mounted in a fluid-filled bag mounted on a movable arm (not shown) that may be placed in contact with a patient, such as that disclosed in U.S. Pat. No. 5,526,814, the disclosure of which is expressly incorporated herein by reference.

In addition, the system 10 may include an imaging device (not shown) for monitoring the use of the system during treatment of a patient. For example, the system 10 may be placed within a magnetic resonance imaging (MRI) device, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

Returning to FIG. 3, during use, a patient 40 may be disposed on the table 30 with water, ultrasonic conducting gel, and the like applied between the patient 40 and the bag 37, thereby acoustically coupling the patient 40 to the transducer 12. The transducer 12 may be focused towards a target tissue region within a tissue structure 42, which may, for example, be a cancerous or benign tumor. The transducer 12 may be activated by supplying a set of drive signals 15 to the transducer 12 to focus ultrasonic energy at the target tissue region 42. The transducer 12 may be activated for sufficient time to substantially necrose the target tissue region 42, e.g., between about 1–20 seconds, and more preferably about 10 seconds or more.

The transducer 12 may be deactivated, for example, for sufficient time to allow heat absorbed by the patient's tissue to dissipate, e.g., between about 45–90 seconds, and more preferably about 60 seconds or more. The transducer 12 may then be focused on another target tissue region (not shown), for example, adjacent to the target tissue region 42, and the process repeated until the entire target tissue structure is ablated.

A system in accordance with the present invention uses control of the oscillation function, e.g., its amplitude, to distribute acoustic energy around a focal plane between both an on-axis focal zone and an off-axis annular-shaped focal zone, i.e., to adjust a relative maximum acoustic intensity level or thermal dose between the two focal zones. In addition or alternatively, the system may control the frequency of the oscillation function to adjust the radius or size of the off-axis annular-shaped focal zone in order to adjust a size of the tissue region being ablated during a single sonication, as described above.

In a further alternative, a similar result may be obtained using a single element transducer, and an acoustic lens disposed between the transducer and its focal plane. The acoustic lens may be divided into segments that may adjust the phase shift value of acoustic energy passing through them. Co-pending application Ser. No. 09/557,185, filed Apr. 21, 2000, the disclosure of which is expressly incorporated herein, discloses an acoustic lens that may provide this desired phase shift control. Alternatively, an acoustic lens may be used, having a varying thickness or that is otherwise processed to provide a continuous phase distribution as a function of position, thereby providing regions causing predetermined phase shift values in acoustic energy passing through the respective regions. In still another alternative, a multiple-element transducer array and an acoustic lens may be used together to provide more complicated phase distributions, as disclosed in the application incorporated above. Thus, using an acoustic lens or other device, the acoustic energy focused at the focal plane may generate a first on-axis focal zone and a second off-axis focal zone, behaving substantially similarly to the electronically controlled system described above.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for performing a therapeutic procedure in a target tissue region of a patient using focused ultrasound, comprising:

a transducer array comprising a plurality of transducer elements disposed about a central axis, each transducer element having an angular position in a circumferential direction about the central axis;

drive circuitry coupled to the transducer elements, the drive circuitry configured for providing respective drive signals to the transducer elements; and a controller coupled to the drive circuitry, the controller configured for controlling the drive circuitry to drive the transducer elements with respective drive signals that have phase shift values based upon the angular position of each respective transducer element, the phase shift values being based upon an oscillation function that oscillates between minimal and maximal phase shift values, and that repeats itself a predetermined number of times about the circumferential direction, the oscillation function having an amplitude defined by a difference between the minimal and maximal phase shift values that is other than an integer multiple of one hundred eighty (180) degrees.

2. The system of claim 1, wherein the transducer array comprises a spherical cap transducer array divided circumferentially into a plurality of sectors comprising the plurality of transducer elements.

3. The system of claim 2, wherein the controller is further configured for controlling the phase shift values of the respective drive signals using a step function that alternates between the minimal and maximal phase shift values for driving alternate sectors about the circumferential direction of the transducer array.

4. The system of claim 3, wherein the minimal phase shift value is zero (0) degrees and the maximal phase shift value is greater than zero (0) degrees and less than one hundred eighty (180) degrees.

5. The system of claim 1, wherein each of the transducer elements has a radial position with respect to the central axis, and wherein the minimal and maximal phase shift values are shifted by a predetermined phase shift based upon the radial positions of respective transducer elements to adjust a focal distance of a focal zone of the transducer array.

6. The system of claim 1, wherein the controller is further configured for controlling the phase shift values such that a first focal zone is created that is located on the central axis, and a second off-axis focal zone is created around the first focal zone.

7. The system of claim 6, wherein the controller is further configured for controlling the phase shift values such that a desired acoustic energy distribution is provided between the first focal zone and the second focal zone.

8. The system of claim 6, wherein the controller is further configured for selecting the predetermined number of oscillations to adjust a radius of the second focal zone.

9. A system for performing a therapeutic procedure in a target tissue region of a patient using focused ultrasound, comprising:
    a transducer array comprising a plurality of transducer elements disposed about a central axis, each transducer element having an angular position in a circumferential direction about the central axis;
    drive circuitry coupled to the transducer elements and configured for providing respective drive signals to the transducer elements; and
    a controller coupled to the drive circuitry, the controller configured for controlling phase shift values of the respective drive signals based upon a step function comprising minimal and maximal phase shift values that are applied to alternate transducer elements about the circumferential direction, the step function having an amplitude defined by a difference between the maximal and minimal phase shift values that is other than an integer multiple of one hundred eighty (180) degrees.

10. The system of claim 9, wherein the minimal phase shift value is zero (0) degrees and the maximal phase shift value is greater than zero (0) degrees and less than one hundred eighty (180) degrees.

11. The system of claim 10, wherein the controller is configured for controlling the step function such that a first focal zone is created that is located on the central axis, and a second off-axis focal zone is created around the first focal zone.

12. The system of claim 11, wherein the controller is further configured for adjusting the minimal and maximal phase shift values of the step function such that a desired acoustic energy distribution is provided between the first focal zone and the second focal zone.

13. The system of claim 11, wherein the controller is further configured for controlling a frequency of the step function such that the step function repeats itself a predetermined number of times about the circumferential direction to adjust a radius of the second focal zone.

14. The system of claim 11, wherein each of the transducer elements has a radial position with respect to the central axis, and wherein the minimal and maximal phase shift values are shifted by a predetermined phase shift based upon the radial positions of respective transducer elements to adjust a focal distance of a focal zone of the transducer array.

15. A method for performing a therapeutic procedure in a target tissue region of a patient using focused ultrasound, the method comprising:
    providing a transducer array comprising a plurality of transducer elements disposed about a central axis, each transducer element having an angular position in a circumferential direction about the central axis;
    driving the plurality of transducer elements with respective drive signals, while substantially focusing ultrasonic energy produced by the plurality of transducer elements towards a focal plane; and
    controlling phase shift values of the acoustic energy generated by each transducer element based upon an oscillation function wherein the phase shift values oscillate between minimal and maximal phase shift values based upon the angular position of the respective transducer element such that a first focal zone is generated that is located on the central axis, and a second off-axis focal zone is generated that is disposed around the first focal zone.

16. The method of claim 15, wherein the minimal phase shift value is zero (0) degrees and the maximal phase shift value is greater than zero (0) degrees and less than one hundred eighty (180) degrees.

17. The method of claim 15, wherein the step of controlling the phase shift values comprises selecting the minimal and maximal phase shift values to adjust a relative maximum acoustic intensity of the first and second focal zones.

18. The method of claim 17, wherein the minimal and maximal phase shift values are selected to optimally distribute acoustic energy between the first focal zone and the second focal zone.

19. The method of claim 15, wherein the transducer array comprises a spherical cap transducer array that is divided circumferentially into sectors comprising the plurality of transducer elements.

20. The method of claim 19, wherein the oscillation function comprises a step function that alternates between the minimal and maximal phase shift values between adjacent sectors about the circumferential direction.

21. The method of claim 15, further comprising controlling the oscillation function such that the oscillation function repeats itself a predetermined number of times about the circumferential direction.

22. The method of claim 21, wherein the predetermined number of times that the oscillation function repeats itself is adjusted to provide a desired radius of the second focal zone.

23. The method of claim 15, wherein the oscillation function approximates a sine wave, and wherein the phase shift value "theta" of each respective transducer element is defined by:

$$\text{"theta"} = \text{"beta"}/2 * (1 - \cos(M * \text{"sai"})),$$

where "beta" is the difference between the maximal and minimal phase shift values, M is an integer representing a number of times that the oscillation function repeats itself about the central axis, and "sai" is the angular position of the respective transducer element.

24. The method of claim 15, wherein each of the transducer elements has a radial position with respect to the central axis, and wherein the minimal and maximal phase shift values are shifted by a predetermined phase shift based upon the radial position of the respective transducer element.

25. The method of claim 15, wherein the step of controlling phase shift values of the acoustic energy comprises driving the transducer elements with respective drive signals that include a phase shift value that oscillates between the minimal and maximal phase shift values based upon the angular position of the respective transducer element.

26. A method for performing a therapeutic procedure in a target tissue region of a patient using focused ultrasound, the method comprising:

providing a transducer including a central axis;

providing an acoustic lens between the transducer and a focal plane, the acoustic lens comprising a plurality of regions or segments disposed about the central axis of the transducer;

driving the transducer with drive signals, while substantially focusing ultrasonic energy produced by the transducer at the focal plane; and allowing the acoustic lens to create phase shifts in the acoustic energy emitted by the transducer and passing through respective regions or segments of the acoustic lens based upon an oscillation function that oscillates between the minimal and maximal phase shift values based upon an angular position of respective regions or segments of the acoustic lens such that a first focal zone is generated that is located on the central axis, and a second off-axis focal zone is generated that is disposed around the first focal zone.

27. The method of claim 26, wherein the acoustic lens has a varying thickness as a function of position, thereby providing the respective phase shifts.

28. The method of claim 26, wherein the step of allowing the acoustic lens to create phase shifts comprises actively controlling segments of the acoustic lens to create the phase shifts in the acoustic energy passing through the respective segments.

29. The method of claim 26, wherein the transducer comprises a multiple element transducer array, and wherein the step of driving the transducer comprises driving the transducer array with drive signals including a predetermined phase shift.

* * * * *